United States Patent [19]
Andrulis, Jr. et al.

[11] Patent Number: 6,140,346
[45] Date of Patent: Oct. 31, 2000

[54] TREATMENT OF CANCER WITH THALIDOMIDE ALONE OR IN COMBINATION WITH OTHER ANTI-CANCER AGENTS

[75] Inventors: Peter J. Andrulis, Jr., Bethesda; Murray W. Drulak, Gaithersburg, both of Md.

[73] Assignee: Andrulis Pharmaceuticals Corp., Bethesda, Md.

[21] Appl. No.: 09/071,813

[22] Filed: May 4, 1998

Related U.S. Application Data

[63] Continuation of application No. 08/471,353, Jun. 6, 1995, abandoned.

[51] Int. Cl.[7] .......... A61K 31/445; A61K 31/66; A61K 31/28; A61K 31/195; A61K 31/13; A61K 33/24

[52] U.S. Cl. .......... 514/323; 514/105; 514/492; 514/561; 514/564; 514/672; 424/649

[58] Field of Search .......... 514/323, 105, 514/492, 561, 564, 672; 424/649

[56] References Cited

U.S. PATENT DOCUMENTS 5,399,363  3/1995  Liversidge et al. .......... 424/490

OTHER PUBLICATIONS

Nguyen et al., Int. J. Oncol., 10(5), 965–969 Abstract Only, 1997.

*Primary Examiner*—Jerome D. Goldberg
*Attorney, Agent, or Firm*—Isaac Angres

[57] ABSTRACT

A method is provided for the treatment of neoplastic diseases in a mammal which comprises administering to said mammal a therapeutically effective amount of thalidomide. The method also uses a combination of thalidomide with other anti-neoplastic agents. Additionally, pharmaceutical compositions containing thalidomide and other anti-cancer agents are also provided.

3 Claims, No Drawings

TREATMENT OF CANCER WITH THALIDOMIDE ALONE OR IN COMBINATION WITH OTHER ANTI-CANCER AGENTS

This application is a continuation of Ser. No. 08/471,353, filed Jun. 6, 1995, now abandoned.

The present invention relates to a novel method for treating cancers with thalidomide alone or in combination with other antiangiogenic and anti-cancer agents. The present invention also relates to methods of treating cancers with cytokine/growth factor inhibitors such as those agents inhibitory to basic fibroblast growth factor (bFGF), Tumor Necrosis Factor alpha (TNF-alpha), and interleukin 1 beta (IL-1 beta) and other antiangiogenic agents as well as pharmaceutical compositions containing thalidomide and/or other antiangiogenesis agents and/or anticancer drugs.

The present invention further relates to a method for ameliorating the symptoms of neoplastic diseases by administering thalidomide alone or in combination with other anti-neoplastic drugs.

The instant invention also relates to a method for inhibiting establishment of neoplastic metastasis by administering thalidomide alone or in combination with other anti-neoplastic drugs.

BACKGROUND OF THE INVENTION

Cancer is second only to cardiovascular disease as a cause of death in the United States. One third of all individuals in the United States will develop cancer and 20% of Americans will die of the disease. In the United States in 1992 there were 26,000 deaths due to malignancies and, of these, half of the deaths were due to the three most common types of cancer lung, breast and colon.

Further, cancer is defined as an abnormal growth of tissue characterized by a loss of cellular differentiation. This term encompasses a large group of diseases in which there is an invasive spread of such undifferentiated cells from a primary site to other parts of the body where further undifferentiated cellular replication occurs, which eventually interferes with the normal functioning of tissues and organs. According to Harrison's *Principles of Internal Medicine,* 13th Edition (McGraw Hill NY, Chap. 317–318, 1994), the terms cancer, neoplasia and malignancy are often used interchangeably in both lay and professional publications.

Cancer is defined by four characteristics which differentiate neoplastic cells from normal ones:

(1) Clonality—Cancer starts from genetic changes in a single cell which multiplies to form a clone of neoplastic cells;

(2) Autonomy—Biochemical and physical factors that normally regulate cell growth, do not do so in the case of neoplastic cells;

(3) Anaplasia—Neoplastic cells lack normal differentiation which occurs in nonmalignant cells of that tissue type;

(4) Metastasis—Neoplastic cells grow in an unregulated fashion and spread to other parts of the body.

Each cancer is characterized by the site, nature and clinical cause of undifferentiated cellular proliferation. The underlying mechanism for the initiation of cancer is incompletely understood; however, 80% of cancers are believed to be triggered by external stimuli such as exposure to certain chemicals, tobacco smoke, UV rays, ionizing radiation and viruses. Development of cancer in immunosuppressed individuals indicates the immune system is an important factor controlling the replication and spread of cancerous cells throughout the body.

The high incidence of cancer in certain families, though, suggests a genetic disposition towards development of cancer. The molecular mechanisms involved in such genetic dispositions fall into a number of classes including those that involve oncogenes and suppressor genes (Vogelstein, et al., *Cell,* 70:523, 1992).

Proto-oncogenes are genes that code for growth promoting factors necessary for normal cellular replication. Due to mutation, such proto-oncogenes are inappropriately expressed—and are then termed oncogenes. Oncogenes can be involved in malignant transformation of the cell by stimulating uncontrolled multiplication.

Suppressor genes normally act by controlling cellular proliferation through a number of mechanisms including binding transcription factors important to this process. Mutations or deletions in such genes contribute to malignant transformation of a cell. Examples of suppressor genes include p53 on chromosome 17, which enables a cell to repair damaged DNA, and DCC on chromosome 18, which normally appears on colon cells enabling them to stick together but is deleted in cancerous colon cells (Cavenee and White, *Scientific American,* 272:72–9, 1995).

Malignant transformation develops and cancer results because cells of a single lineage accumulate defects in certain genes such as proto-oncogenes and suppressor genes responsible for regulating cellular proliferation. A number of such specific mutations and/or deletions must occur in a given cell for initiation of uncontrolled replication. It is believed that genetic predisposition to a certain type of cancer results from inheritance of genes that already have a number of mutations in such key regulatory genes and subsequent exposure to environmental carcinogens causes enough additional key mutations or deletions in these genes in a given cell to result in malignant transformation (Nowell et al., *Science,* 194:23–8, 1976). Changes in other types of genes could further the ability of tumors to grow, invade local tissue and establish metastases at distant body sites.

Cancers can produce clinical symptoms in three general ways:

1) Obliteration of normal tissues with concomitant interference with normal tissue function, as cancerous cells proliferate. This local expansion of cancerous tissue can result in pain due to pressure on or stretching of nerve fibers;

2) Excessive or inappropriate production of biologically active agents by cancerous cells such as cytokines or hormones. This can result in clinical illness. Such agents are important because they may serve as markers for a certain tumor type, may produce symptoms themselves and may serve to promote direct tumor growth;

3) Psychological effects upon the patient.

Early detection of cancer by the clinician depends on his awareness of the patient's family history with respect to different types of cancer, possible exposure of the patient to environmental factors that cause cancer combined with manifestation of any of the seven common warning signs of cancer:

1) change in bowel or bladder habits;

2) a sore that does not heal;

3) unusual bleeding or discharge;

4) thickening or lumps in the breast or elsewhere;

5) obvious change in a wart or mole;

6) nagging cough or hoarseness;

7) indigestion or difficulty in swallowing.

The diagnosis of cancer is primarily made by histologic and cytologic examination of tumor specimens to exclude benign tumors, hyperplasia and inflammatory processes. After a diagnosis of cancer is made, the description of the malignancy should include three characteristics that classify the neoplasm, yield information important to prognosis and, together with determining the anatomic extent of tumors (staging), help select optimal therapy:

1) Tissue of origin of the cancer;

2) Anatomic origin of the cancer;

3) Degree of cellular differentiation of the tumor.

With most solid tumors, it is the metastatic encroachment of the tumor on ohter vital function that causes the demise of the patient. Approximately 30–40% of patients at initial diagnois have metastatic disease; once this occurs, there is a relentless progression of the disease. Invasion is a prerequisite for migrationof tumor cells in connective tissue stroma and baseement membranes form the major physical barriers to the migration process.

This local extracellular matrix (ECM) invasion is the initial event in the development of metastasis although the rate limiting step in the often prolonged natural history of tumor metastasis is unknown. The sequential biochemical mechanism first invovles cell attachment to specific components of ECM followed by progressive protolytic dissolution.

The signaling pathways that intiate tumor cell migdration are mong the least understood aspects of invasion and metastasis, but are believed to result from specific ligand-receptor interactions. Phospholipase $A_2$ ($PLA_2$) is akey membrane signaling enzyme that modulates the level of available arachidonic acid, the substrate required for the production of eicosanoids (e.g., prostaglandin's leukotrienes, and thromboxanes). These pro-inflammatory mediators have been implicated as initiators of metastasis in primary neoplastic tissue. Inhibition of $PLA_2$ has been suggested as a novel means to control chronic inflammation associated with tumor progression.

Cancer therapy is currently divided into five subspecialties: (1) surgery, (2) radiation therapy, (3) chemotherapy, (4) immunotherapy, and (5) anti-angiogenic therapy.

Surgery was the first and, in a number of cases, still the only effective therapy in many of the common solid tumors. However, surgery alone has been proven to be effective in treating only 25% of tumors. Most often surgery is used as a means of reducing the size of a tumor and is used in combination with other therapeutic approaches.

Radiation therapy acts by delivering ionizing electromagnetic radiation to a tumor site. Electromagnetic radiation, termed external beam radiation, is delivered externally to a body site from an outside source, while in bradytherapy radiation is delivered by insertion of radioactive materials within the body at the site of the tumor.

In radiation-induced cell death, reactive oxygen intermediates and free radicals are produced by exposure to the radiation. The utility of radiation depends on the inherent radiosensitivity of a given tumor versus adjacent normal tissue with the presence of oxygen in the tumor being an important determinant of radiosensitivity. Oxygen free radicals produced from the oxygen in the tumor by exposure to radiation damages cellular components, especially DNA. Radiation therapy has both short and long-term sequelae. Acute sequelae are self limited and include erythema and desquamation of skin; anemia, myelosuppression and gastrointestinal upset. Long-term sequelae can be progressive and include myelitis, pericarditis, stenoses, hepatitis, and nephropathy.

At the moment, chemotherapy is the primary treatment used for disseminated malignant disease. Often the tumor burden is initially reduced by surgery followed by chemotherapy whose goal it is to eliminate the undetectable micrometastasis which remain. Death of malignant cells by chemotherapy is dependent on the exposure time to the chemotherapeutic agent and its concentration, both of which are limited due to toxicity. In combination therapy, agents should have different mechanisms of action on tumor cells to complement each other and prevent resistance from developing. The following are a number of different groups of chemotherapeutic agents which are used alone or in combination to treat various cancers:

1) Antimetabolites: compounds that induce cytotoxicity in tumor cells by being false substrates in biochemical pathways which results in interference with important cellular functions. Examples include aminopterin, hydroxyurea, methotrexate, pyrimidine analogue antimetabolites such as fluorouracil and cytarabine, and purine analogue antimetabolites such as six-mercaptopurine, fludarabine, pentostatin and chlorodeoxyadenosine. High dosages of these drugs may be associated with acute renal damage, hepatotoxicity and gastrointestinal toxicity.

2) Plant alkaloids: vinca alkaloids such as vincristine and vinbiastine; the taxanes such as taxol; and the epipodophyllotoxins such as etoposide and teniposide. These substances may induce neurotoxicity, bone marrow hyperplasia and hypersensitivity reactions.

3) Anti-tumor antibiotics: anthracyclines such as doxorubicin, daunorubicin, idarubicin, and epirubicin; anthracenediones such as mitoxantone; cytotoxic glycopeptides such as bleomycin, mitomycin and dactinomycin. This group of compounds has been demonstrated to induce cardiomyopathy, tissue extravasation, chronic interstitial pneumonitis, renal failure, gastrointestinal toxicity and myelosuppression.

4) Alkylating agents: compounds that inhibit DNA synthesis by forming covalent bonds with nucleic acids. This group includes mechlorethamine, cyclophosphamide, ifosamide, melphalan, chlorambucil, busulfan, and thiotepa as well as nitrosurea alkylating agents such as carmustine and lomustine and platinum compound alkylating agents such as cisplatin and carboplatin. The most common dose-limiting toxicity of these compounds is myelosupppression. Alkylating agents have also been known to induce secondary leukemias, neurotoxicity, myocardial necrosis and nephrotoxicity;

5) Endocrine therapy: adrenocorticosteroids such as prednisone, methylprednisone and dexamethasone; androgens such as fluoxymesterone; anti-androgens such as flutamide; estrogens such as diethylstilbestrol and ethinyl estradiol; anti-estrogens such as tamoxifen; progestins such as medroxyprogesterone and megastrol acetate; aromatase inhibitors such as aminoglutethimide; gonadotropin-releasing hormone agonists such as leuprolide and somatostatin analogues such as oct-reotide. Endocrine therapy maybe accompanied by neurotoxicity, metabolic derangements such as hyperglycemia, hypokalemia, fluid retention, hepatotoxicity, impotence, amenorrhea, nausea and maculopapular rash;

6) Other agents: dacarbazine, procarbazine and L-asparaginase.

Drug resistance exhibited by tumors is the most important cause of treatment failures. Such resistance is either de novo in nature where tumors are inherently resistant to chemotherapy, or acquired, upon exposure to a chemotherapeutic agent. In the later instance, a tumor undergoes further spontaneous mutations resulting in a population of genetically heterogeneous cells as it grows from a single malignantly transformed cell. This heterogeneity applies to the extent individual cells in the tumor are susceptible to the chemotherapeutic agent as well. Treatment with a given agent will eliminate all the susceptible cells from the tumor and select for those cells that are resistant to the agent. To maximize success in treating such tumors it is important to initially reduce the tumor size by surgery and then use combination chemotherapy involving agents with distinctly different mechanisms of action.

Another facet of this combination approach to cancer therapy that may produce an answer to this issue of drug resistance is immunotherapy. The basic assumption here is that since tumor cells have antigens unique to the tumor on their surface, it may be possible to assist the host's immune system to more effectively respond to them and thereby destroy the cancer. A number of approaches have been used. For example, attempts have been made by a number of investigators to increase the antigen-specific immune response to the tumor by immunizing the host with cells originally taken from his tumor along with BCG. Hoover and Hanna (*Semin. Surg. Oncol.*, 5:436–440, 1989) reported that such a vaccine had a therapeutic effect in the treatment of colon cancer.

Cytokines such as interferon or interleukin 2 (IL-2) alone or with lymphokine-activated killer cells have been used as cancer therapeutics. Interferon-alpha has proven to be effective in treating hairy cell leukemia (Golomb et al., *Hematology*, 4thd ed., NY McGraw Hill, pgs. 1025–30, 1990, Quesada et al., *N. E. J. M.*, 310:15–18, 1984) and for AIDS-associated Kaposi's Sarcoma (Real et al., *J. Clin. Oncol.*, 4:544–551, 1986). IL-2 has been used in vitro to stimulate and develop natural killer cells taken from a cancer patient. Such cells are then reinfused back into the patient and have acted as an effective cancer therapy in renal cell carcinoma and melanoma (Greenberg, *Adv. Immunol*, 49:281–355, 1991; Yabro, *Semin. Surg. Oncol.*, 7:183–191, 1991). It is believed that IL-2 stimulates interferon gamma production, which in turn, induces genes that code for major histocompatibility class I and class II antigens that are essential for tumor antigen presentation leading to an adequate immune response (Janik, from *Clinical Applications of Cytokines* J. J. Oppenheim et al Editors, Oxford Univ. Press, NY, 1993). Another approach employing cytokines as anticancer therapeutics involves delivering cytokines continuously to the tumor by transfecting tumor cells in vitro with genes that code for cytokines so they can produce these cytokines when reinfused back into the patient. Tepper et al. (*Cell*, 57:503–12, 1989) studied the introduction of the IL-4 gene into several tumor cell types. The problem encountered, however, was that many cytokine-producing cells failed to grow when infused into animals. However, Golumbek et al. (*Science*, 254:713–6, 1991) showed that tumor cells expressing IL-4 were able to cause tumor regression in animals, thereby validating this approach. Kedar and Klein (*Adv. Cancer Res.*, 59:245–322, 1992) modified this approach by obtaining T cells that had infiltrated a tumor, exposing them to IL-2 in vitro, and reinfusing them into the same patient. Although this approach has shown promise, it is limited by difficulties in obtaining and expanding the cytotoxic T cell populations needed. Cytokine therapy in general has not been as effective as hoped for in the treatment of cancer because under natural conditions cytokines are produced and act in synchrony with one another; to administer one cytokine in high doses upsets the natural balance and can result in many unforeseen effects on other cytokines and more generally the host (Janik, from *Clinical Applications of Cytokines* J. J. Oppenheim et al Editors Oxford Univ. Press, NY, 1993).

The difficulty in working with cytokines is that they can facilitate cancer as well as treat it. It is well known that in order for tumors to grow and spread, they must have an adequate blood supply, so angiogenesis is a necessary part of a cancer's progression (Folkman, *J. Natl. Cancer Inst.*, 82:4–6, 1990). Further, the continuous stimulation of neovascularization is also a prerequisite for metastasis (Weidner et al., *N.E.J.M.*, 324:1–8, 1991). Tumor angiogenesis may be mediated by dysregulation of certain cytokines which play a role in the normal angiogenic process (Rosen, *EXS*, 65:301–10, 1993). Angiogenesis involves a series of discrete steps commencing with the formation of new capillaries derived from the existing microvasculature (Folkman, *Adv. Cancer Res.*, 43:175–203, 1985). Initially, protease degradation of the basement membrane of the parent blood vessel enables endothelial cell migration into the tissue in response to an angiogenic stimulus. These migrating endothelial cells differentiate into a lumen or sprout which increases in length with time as endothelial cells proliferate. Since there are a series of discrete steps involved in angiogenesis, this has presented a opportunity for development of a number of therapies each with a markedly different mechanism of action. Optimal anti-angiogenic therapy, therefore, may involve multiple therapeutic interventions at the different steps of angiogenesis.

The following are examples of some of these cytokine-based approaches to anti-angiogenic and/or cancer therapy:

1) Agents such as lisofylline (CT1501R) and CT2584 inhibit tumor angiogenesis by interfering with the lipid second messenger phosphatidic acid which is common to both angiogenic growth factors and autocrine tumor growth factor production;

2) Antibodies against the transmembrane glycosylated 185 KD tyrosine kinase of erbB2 oncogene neu. Amplification of erbB2 has an adverse effect in patients with breast cancer (Slamon et al., *Science*, 235:177–82, 1987). An antibody against p185 causes transformed neu cells to revert to a nontransformed phenotype. Growth of tumor xenografts were inhibited by a monoclonal antibody to p185 in a dose dependent manner (Drebin et al., *Proc. Natl. Acad. Sci. (USA)*, 83:9129–33, 1986). An antibody to the product of erbB2 can inhibit proliferation of breast adenocarcinoma cells which express elevated levels of p185 (Kumar et al., *Mol. Cell Biol.* 11:979–86, 1991);

3) Protease inhibitors such as Batismastat (BB94), an anti-metalloprotease, as well as cartilage and eye-derived protease inhibitors. Each inhibits proteases involved in a number of steps of angiogenesis including degradation of the basement membrane of parent venules to facilitate endothelial cell escape during capillary sprouting and migration (Moses and Langer, *Biotechnology*, 9:630–34, 1991);

4) Antibodies against the tumor vasculature itself, such as antibody to vitronectin (integrin avB3) which blocks interaction between this receptor and matrix proteins resulting in apoptosis of dividing immature endothelial cells;

5) Inhibitors to such heparin binding growth factors as the fibroblast growth factors (FGF), which are involved in tumor growth and/or angiogenesis. The affinity of FGF for heparin regulates their function in vivo. Heparin produced by vascular endothelial cells (Nader et al., *Proc. Natl. Acad. Sci. (USA)*, 84:3565–9, 1987) can break down into low molecular weight degradation products (Vannucchi et al, *Biochem. Biophys. Res. Commun.*, 140:294–301, 1986). It is believed that such degradation products act as a heparin transport system for FGF's into endothelial cells (Folkman and Ingber, In *Angiogenesis: Regulatory Role of Heparin and Related Molecules*, Lane, Lindahl Editors London: Edward Arnold, 317–333, 1989). Agents such as pentosan polysulfate, platelet factor 4 ($PF_4$) and protamine act as inhibitors of such heparin-binding growth factors, such as FGF's by binding to heparin and thus preventing it from growth factor binding (Folkman and Shing, *Adv. Exp. Med. Biol.*, 313:355–64, 1992). Chick embryo and rabbit cornea animal models have demonstrated that such agents inhibit angiogenesis (Taylor et al., *Nature*, 297:307–12, 1982) and tumor growth in animals (Maione, *Science*, 247:77–9, 1990; *Cancer Res.*, 51:2077–2083, 1991);

6) Angiostatic steroids are combinations of heparin derivatives and glucocorticosteroids which inhibit capillary endothelial cell proliferation (Sakamoto et al., *Cancer J.*, 1:55–58, 1986); and tumor extracts from animals treated with the two substances can inhibit endothelial cell migration (Rong et al., *Cancer*, 57:586–90, 1986). One mechanism of action for these angiostatic steroids maybe by influencing endothelial cell migration and proliferation or by dissolving the basement membrane resulting in a loss in capillary viability (Ingber et al., *Endocrinology*, 119:1768–75, 1986);

7) Thrombospondin is a 140 KD protein that inhibits angiogenesis in vivo in the the corneal pocket assay and capillary endothelial cell migration in vitro (Good et al., *Proc. Natl. Acad. Sci. (USA)*, 87:6624–8, 1990). Thrombospondin has a high affinity for heparin derivatives (Folkman and Shing, *Adv. Exp. Med. Biol.*, 313:355–64, 1992).

8) Cytokines such as IL-12 which exhibit preliminary evidence of an inhibitory effect on angiogenesis.

In addition to the previously cited angiogenic interventions used to treat cancer, applicants have developed a novel approach to antiangiogenic therapy which is based on the role of IL-1 beta, TNF alpha and basic FGF (bFGF) play in tumor development and angiogenesis.

IL-1 beta and TNF-alpha can stimulate tumor cell mobility and invasiveness by eliciting the expression of plasminogen activators in tumor cells. Such plasminogen activators convert latent proenzyme plasminogen into plasmin, a serine protease that degrades the basement membrane of the microvasculature and facilitates tumor cell spread from the blood into adjacent tissues (Rosen et al., *EXS*, 65:301–10, 1993). Further TNF-alpha also stimulates endothelial cell motility in vitro (Leibovich, *Nature*, 329:630–632, 1987; Rosen et al., from *Cell Motility Factors*, Goldberg and Rosen, Editors Verlag, Basel, pg. 194–205, 1991) and demonstrates strong angiogenic activity in vivo (Leibovich et al., *Nature*, 329:630–632, 1987; Frater-Schroder et al., *Proc. Natl. Acad. Sci. (USA)*, 84:5277–5281, 1987). IL-1 beta and TNF-alpha are important factors in in vitro induction of the endothelial cell-leukocyte receptor E-selectin (Bevilacqua et al., *Science*, 243:1160–65, 1989), VCAM1 (Elices et al., *Cell* 60:577–84, 1990) and ICAM (Rothein et al., *J. Immunol*, 137:1270–4, 1986); and of dermal vasculature in vivo. It is believed that expression of macrophage receptors on the surface of endothelial cells facilitates the binding of these cells that is the precondition to transendothelial migration. Once in the tissues, macrophages are believed to act as an angiogenic stimulus by secreting angiogenic substances such as bFGF (Frater Schroder et al., *Proc. Natl. Acad. Sci. (USA)*, 84:5277–5281, 1987). Gross et al. (*J. Natl. Cancer Inst.*, 85:121–131, 1993) showed that bFGF stimulates proliferation in some tumor cells and facilitates tumor vascularization.

Thalidomide has been shown to inhibit TNF-alpha production in erythema nodosum leprosum patients (Sarno et al., 1991) and in vitro stimulated monocytes (Sampaio et al., *J. Exp. Med.*, 173:699–703, 1991). Shannon et al. (*Amer. Soc. for Microbiology Ann. Meeting*, Abst. U-53, 1990) indicated thalidomide inhibited IL-1 beta production in vitro. Furthermore, D'Amato et al. (*Proc. Natl. Acad. Sci. (USA)*, 91:4082–5, 1994) demonstrated that thalidomide was an effective inhibitor of angiogenesis induced by bFGF in the rabbit cornea micropocket assay. In light of thalidomide inhibitory activity on IL-1 beta, TNF-alpha and bFGF and the role these cytokines to play in angiogenesis, the purpose of this invention is to use thalidomide alone or in combination with other anti-cancer and/or anti-angiogenic therapies to treat cancer. An example of such combination therapy could involve thalidomide given with pentoxifylline and a glucocorticoid such as dexamethasone. The activity of each of these agents would be expected to enhance that of the other two in inhibiting TNF-alpha synthesis since each of these agents acts as a inhibitor at a different point in this synthesis. Pentoxifylline inhibits TNF-alpha gene transcription (Doherty et al., *Surgery*, 110:192, 1991), while thalidomide enhances TNF-alpha m-RNA degradation (Moreira et al., *J. Exp. Med.*, 177:1675–80, 1993) and glucocorticoids such as dexamethasone inhibit TNF-alpha m-RNA translation (Han et al. *J. Exp. Med.*, 172:391, 1990).

Thalidomide was first synthesized and marketed in the 1950's as a sedative. The toxicity of the compound was so low that a dose killing 50% of animals ($LD_{50}$) could not be established. Thalidomide was therefore thought to be a safer alternative to barbiturates. In 1961 thalidomide administered to pregnant women resulted in an epidemic of congenital malformations. The incidence of malformed babies paralleled the sales of thalidomide and quickly dropped off when thalidomide was removed from the market.

Oral administration of thalidomide in the range of 100–200 mg in adult humans results in a peak blood level of 0.9–1.5 mg/liter after 4–6 hours. Hydrolytic cleavage of thalidomide occurs in vitro, the rate of which increases as the pH increases. However, hydrolytic cleavage of thalidomide in serum is much slower than in vitro at pH 7.4. This may be due to thalidomide being highly bound to plasma proteins. Studies in animals demonstrated high thalidomide concentrations in the gastrointestinal tract, liver and kidneys with lower concentrations in muscle, brain and adipose tissue. In pregnant animals, thalidomide can pass across the placenta. Although a complete study of thalidomide metabolism in humans has not been performed, in animals the main pathway for thalidomide breakdown appears to be nonenzymatic hydrolytic cleavage.

Even though immunodulatory effects of thalidomide have not been clearly defined at the molecular level, thalidomide has been used to treat a number of immunologically based diseases such as: aphthous ulcers (Jenkins et at., *Lancet*, 2:1424–6, 1984; Grinspan, *J. Amer. Acad. Dermatol*, 12:85–90, 1985; Revuz et al., *Arch. Dermatol*, 126:923–7, 1990), Graft vs Host Disease (Lim et al., *Lancet*, 1:117, 1988; McCarthy et al., Lancet, 2:1135, 1988; Henley et al., Lancet, 2:1317, 1988), erythema nodosum leprosum (Sheskin, Lepr. Rev., 36:183–7, 1965; Sheskin and Convit, Int. J. Lepr., 37:135–46, 1969; Pearson and Vedagiri, Lepr. Rev., 40:111–6, 1969), Behcet's syndrome (Saylan and Saltik, Arch. Dermatol 118: 536, 1982; Jorizzo et al., Arch. Int. Med., 146:878–81, 1986), actinic prurigo (Londono, Int. J. Dermatol, 12:326–8, 1973; Lovell et al., Brit. J. Dermatol, 108:467–71, 1983), ulcerative colitis (Waters et al., Brit. Med. J., 1:792, 1979) and discoid lupus erythematosus (Knop et al., Arch. Dermatol Res., 271:165–70, 1981). In these studies, dosages of thalidomide ranging from 100 mg/day to 800 mg/day were administered without serious side effects.

SUMMARY OF THE INVENTION

The primary objective of the present invention is to provide a method for the treatment of angiogenesis accompanying cancer with antiangiogenic agents, including inhibitors of cytokines and growth factors.

A further objective of the present invention is the treatment of cancers with thalidomide alone or in combination with other agents that inhibit angiogenesis, including cytokines and growth factors, and/or with other classes of anticancer therapeutics.

Another objective of the current invention is to provide a method for treating cancer with thalidomide at a given regimen.

An additional objective of the current invention is to provide compositions of matter comprising one or more antiangiogenic agents and/or cytokine and/or growth factor inhibitors with one or more anticancer therapeutics.

A further objective of the present invention is a method for the treatment of cancers which comprises therapy with thalidomide and other drugs on alternative days by diverse schedules.

An additional objective of the current invention is to utilize thalidomide alone or in combination with other antiangiogenic agents, including cytokine and growth factor inhibitors and/or other cancer treatments as a maintenance therapy to prevent the relapse of cancer.

A still further objective of this invention is to use thalidomide alone or in combination with other angiogenesis and/or cytokine or growth factor inhibitors and/or other cancer treatments as prophylactic therapy for individuals believed to be susceptible to developing a certain type of cancer.

Another objective of the present invention is to provide a method for inhibiting the establishment of cancer metastases by administering thalidomide alone or in combination with other chemotherapeutic agents.

Another further objective of the present invention is to provide a method for treating Kaposi's Sarcoma by administering thalidomide either orally or topically.

DESCRIPTION OF THE PREFERRED EMBODIMENTS

Within the context of the present specification, applicant will use the terms cancer and neoplasms interchangeably and their meaning is intended to be the same. Accordingly, the present invention is directed to a method for the treatment of neoplastic diseases in a mammal which comprises administering to said mammal a therapeutically effective amount of thalidomide.

The instant invention is more particularly directed to a method for the treatment of solid neoplasms in a mammal which comprises administering to said mammal a therapeutically-effective amount of an inhibitor selected from the group consisting of basic fibroblast growth factor (bFGF) inhibitors, tumor necrosis factor alpha (TNF-alpha) inhibitors and Interleukin-1 beta (IL-1 beta) inhibitors.

In another aspect of the invention, a method is provided for the inhibiting the establishment of neoplastic metastasis in a mammal afflicted with a neoplastic condition which comprises administering to said mammal a therapeutically-effective amount of thalidomide to inhibit said tumor development.

The invention also provides a method for the treatment of Kaposi's sarcoma in a patient which comprises administering to said afflicted patient a therapeutically-effective amount of thalidomide.

The therapeutic treatment with thalidomide can utilize any type of administration including oral administration, topical application, intramuscular injection and intravenous infusion. The effective dose per kg of body weight may be determined for example by chemosensitive assays utilizing cells derived from the patient neoplasms. A typical therapeutic dose is about 100 mg to 1200 mg/kg of thalidomide for a typical body weight of 70 kg.

In another embodiment, applicants provide a pharmaceutical composition of matter suitable for treating and inhibiting the spread of cancer comprising: (a) a therapeutically effective amount of thalidomide; (b) a effective amount of an anticancer drug selected from the group consisting of antimetabolites, plant alkaloids, anti-tumor antibiotics, alkylating agents, endocrinologic drugs and miscellaneous anticancer agents and (c) effective amounts of another TNF alpha, IL-1 beta and bFGF inhibitors.

Suitable antimetabolites are compounds that induce cytotoxicity in tumor cells by being false substrates in biochemical pathways which results in interference with important cellular functions. Examples of antimetabolites are aminopterin, hydroxyurea, methotrexate, pyrimidine analogue antimetabolites such as fluorouracil and cytarabine, and purine analogue antimetabolites such as six-mercaptopurine, fludarabine, pentostatin, and chlorodeoxyadenosine.

The preferred plant alkaloids consist of vinca alkaloids such as vincristine and vinblastine; the taxanes such as taxol; and the epipodophyllotoxins such as etoposide and teniposide.

Suitable anti-tumor antibiotics include the anthracyclines such as doxorubicin, daunorubicin, idarubicin, and epirubicin; antracenediones such as mitoxantone; cytotoxic glycopeptides such as bleomycin, mitomycin and dactinomycin.

Alkylating agents which can be used are compounds that inhibit DNA synthesis by forming covalent bonds with nucleic acids. This group includes mechlorethamine, cyclophosphamide, ifosamide, melphalan, chlorambucil, busulfan, and thiotepa as well as nitrosurea alkylating agent such as carmustine and lomustine and plantinum compound alkylating agents such as cisplatin and carboplatin.

Compounds suitable for endocrine therapy includes adrenocorticosteroids such as prednisone, methylprednisone and dexamethasone; androgens such as fluoxymesterone; anti-androgens such as flutamide; estrogens such as diethylstilbestrol and ethinyl estradiol; anti-estrogens such as tamoxifen; progestins such as medroxyprogesterone and megastrol acetate; aromatase inhibitors such as aminoglutethimide; gonadotropin-releasing hormone agonists such as leuprolide and somatostatin analogues. Endocrine therapy may be accompanied by neutrotoxicity or metabolic derangements such as hyperglycemia, hypokalemia, fluid retention, hepatotoxicity, impotence, amenorrhea, nausea and maculopapula rash.

Other miscellaneous agents which include dacarbazine, procarbazine and L-asparaginase.

The instant invention is also directed to a method for inhibiting the spread of malignant neoplasms selected from the group consisting of lung and breast neoplasms, prostatic carcinoma, brain cancer, as well as other cancers in a mammal in need thereof which comprises administering to said mammal an effective amount of thalidomide alone or in combination with other anti cancer agents. Other cancers contemplated within the scope of the invention include colonic, GI, pancreatic, uterine, ovarian, endometrial, bone or any other cancer of epithelial or connective tissue cell origin.

When used alone, the therapeutically effective amounts of thalidomide are typically 50 mg to 1000 mg and preferably 100 mg to 750 mg one to three times a day for a sufficient period of time to induce shrinkage or remission of the cancer.

Under certain circumstances, it is desirable to administer thalidomide therapy simultaneously with other anti-cancer drugs. For example, 500 mg of thalidomide can be administered three times a day while the patient is being given a chemotherapeutic treatment with carmustine, i.e., 150–200 mg/m$^2$ every six weeks.

If Lomustine is given orally, typically 130 mg/m$^2$ in a single oral dose is given every six weeks while the patient is in thalidomide therapy. When bleomycin is the drug of choice, 10 to 20 units/m$^2$ IV is given daily for five days every three weeks. The therapy with all of the above chemotherapeutic compounds is given concurrently or separately with thalidomide. In an alternate embodiment, thalidomide is administered every other day.

The precise amount of thalidomide alone or in combination With other chemotherapeutic agents mentioned above will vary depending, for example, on the condition for which the drug is administered and the size and kind of the mammal. Generally speaking the thalidomide can be employed in any amount effective in the treatment of cancers.

For humans, typically effective amounts of thalidomide for use in the unit dose compositions of the present invention range form 50 mg to 1200 mg per 24 hours; however, greater amounts may be employed if desired. This range is based on administration to a 70 Kg human. A preferred amount is 100 to 1500 mg per 24 hour period. Of course, the amounts of each compound selected will depend on the weight of the mammal and the disease state. One skilled in the art can adjust the dosage forms to achieve the desired therapeutic levels.

The compound of the present invention can be prepared and administered in a wide variety of oral, topical and parenteral dosage forms. It will be obvious to those skilled in the art that the following dosage forms may comprise as the component, either thalidomide alone or in combination with other compounds.

Preferably the compounds of the present invention are administered orally, cutaneously, intramuscularly, subcutaneously, or intravenously.

For preparing pharmaceutical compositions from the compounds of the present invention, pharmaceutical acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders, capsules and tablets preferably contain from five or ten to about seventy percent of the active compound. Suitable carriers are magnesium carbonate, magnesium stearate, talc, sugar, lactose, pectin, dextrin, starch gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration. Lotions, ointments, or suspensions can be used as dosage forms for topical application.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid for preparations include solutions, suspension, emulsions, for example, water or water propylene glycol solutions or DMSO solutions. For parenteral injection, liquid preparations can be formulated in solution in aqueous polyethylene glycol solution or DMSO-water solutions.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid for preparation for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, lotions, ointments and powders in vials or ampoules. Also, the unit dosage form can be a capsule, tablet, cachet, lotion, ointment, or lozenge itself, or it can be the appropriate number of any of these in packaged form.

It is also possible to administer thalidomide in a time-release formulation. A wide variety of methods are now available in the art for preparing time-release or long-acting compositions. Any of these time-release or long-acting formulations are suitable in the practice of the present invention as long as it does not adversely affect the effectiveness of the thalidomide in the treatment of the cancer. Advantages of time-release formulations include a lower concentration of peak serum absorption which substantially reduces the adverse side effects and toxicity of the compound administered. In addition, a reduced frequency of administration results, which substantially improves patient compliance. A frequency of administration of every 12 to 24 hours would be preferred. In addition, more constant serum concentration of thalidomide would result thereby allowing a more consistent relief of symptoms.

The following examples, not to be construed as limiting, illustrate formulations which can be made according to the invention.

EXAMPLE 1

500 mg of thalidomide are mixed with 130 mg of lomustine. The active ingredients are triturated and q.s. with lactose to selected capsules size.

EXAMPLE 2

500 mg of thalidomide are mixed with 375 mg of cyclophosphamide. The active ingredients are triturated and q.s. with lactose to selected capsule size.

EXAMPLE 3

250 mg of thalidomide are mixed with 100 mg of taxol. The active ingredients are triturated and q.s. with lactose to selected capsule size.

The following Examples further illustrate the usefulness of the invention.

EXAMPLE 4

750 mg of thalidomide are mixed with 100 mg of tamoxifen. The active ingredients are triturated and q.s. with lactose into selected capsule size.

EXAMPLE 5

Hard gelatin capsules are prepared using the following ingredients

| Thalidomide | 250 |
|---|---|
| Starch dried | 200 |
| Magnesium stearate | 10 |

The above ingredients are mixed and filled into hard gelatin capsules in 460 mg quantities.

EXAMPLE 6

A tablet formula is prepared using the ingredients below

| Thalidomide | 250 |
|---|---|
| Cellulose, microcrystalline | 400 |
| Silicon dioxide, fumed | 10 |
| Stearic acid | 5 |

The components are blended and compressed to form tablets each weighing 665 mg.

EXAMPLE 7

Tablets each containing 60 mg of active ingredient are made up as follows:

| Thalidomide | 60 mg |
|---|---|
| Starch | 45 mg |
| Microcrystalline cellulose | 35 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 8

Capsule each containing 80 mg of medicament are made as follows:

| Thalidomide | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 9

Suspensions each containing 50 mg of medicament per 5 ml dose are made as follows:

| Thalidomide | 50 mg |
|---|---|
| Sodium carboxymethylcellulose | 50 mg |
| Syrup | 1.25 ml |
| Benzoic acid solution | 0.10 ml |
| Flavor | q.v |
| Color | q.v |
| Purified water to | 5 ml |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

EXAMPLE 10

Capsules each containing 150 mg of medicament are made as follows:

| | |
|---|---|
| Thalidomide | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

The thalidomide alone or in combination with other therapeutic agents can also be formulated in liposomal form. The liposomal-encapsulated thalidomide composition of the present invention also represents a novel approach in cancer therapy.

The liposome-encapsulated material can be obtained by dissolving thalidomide in a solvent. The solvent used is preferably a polar organic solvent, e.g., methanol or ethanol. When the thalidomide is completely dissolved in the solvent, the dissolved thalidomide is complexed with cardiolipin by adding a solution of cardiolipin to the solvated chemotherapeutic agent. The solvent used to dissolve the cardiolipin can be methanol or ethanol.

The mixture obtained is then stirred gently and evaporated under an inert atmosphere to dryness. The inert atmosphere can be nitrogen, argon, or combination of these two.

To this dried mixture, one then adds phosphatidylcholine, cholesterol, and either phosphatidylserine or dicetylphosphate (DCP). The mixture obtained is then stirred gently to achieve a homogeneous solution and evaporated to dryness under an inert atmosphere to produce lipids and drug films.

The dried lipids are then resuspended in a solution where they are hydrated and then sonicated. The solution used can be a saline solution, a phosphate buffered saline, a lactose solution, a glucose solution, a mannitol solution, or any other known physiologic buffered solution. Non-entrapped thalidomide is separated from the liposome-encapsulated thalidomide by dialysis and/or high speed centrifugation.

If desired, the liposome encapsulated thalidomide can then be lyophilized to permit storage. If the liposome-encapsulated thalidomide is stable in solution, however, it can be stored in a saline or lactose medium.

In the above preparation, the relative amounts of the components used to prepare the liposome-encapsulated thalidomide are as follows. The thalidomide is used in an amount of from 6.8 parts by weight to 9.2 parts by weight. The cardiolipin is used in an amount of from 30.6 parts by weight to 41.4 parts by weight. The phosphtidylcholine is used in an amount of form 102 parts by weight to 138 parts by weight. The cholesterol is used in an amount of from 34 parts by weight to 46 parts by weight. And the phosphatidylserine or dicetyphosphate is used in an amount of from 6.8 parts by weight to 9.2 parts by weight.

Those liposome-encapsulated chemotherapeutic compositions are useful in the treatment of solid cancers such as lung, breast prostate, colon, GI and others. In the treatment of these tumors, the liposome-encapsulated chemotherapeutic agent dissolved in an appropriate pharmaceutical carrier or excipient is administered intravenously either as a bolus or continuously over a period of from 5 minutes to 30 minutes. In continuous administration, the liposome-encapsulated therapeutic agent suspended in an appropriate pharmaceutical carrier or excipient can be delivered by osmotic pump.

Carriers which can be used in the present invention include suitable pharmaceutically-acceptable carriers comprising excipients and auxiliaries which facilitate processing of the active compounds into preparations which can be used pharmaceutically. Suitable formulations for intravenous administration of the active compound may include suspensions of the active ingredients.

Solutions for administration intravenously contain from about 0.1 to about 99.5% by weight, and preferably from about 25 to 85% by weight of active ingredients, together with the excipient.

The dose and the route of administration and the carrier and/or adjuvants used may vary based on the tumor type being treated and in view of known procedures for treatment of such tumors.

EXAMPLE 11

Liposomal Encapsulation

To encapsulate thalidomide in liposome, various lipid constituents were investigated and percent efficiency of the drug entrapped in liposomes was determined. The best combination of lipids which is developed in our laboratories is as follow:

Thalidomide 8 mg, was dissolved in methanol and stirred gently to achieve a clear solution, and was complexed with 36 mg of cardiolipin in ethanol. The mixture was stirred gently and evaporated under $N_2$ to dryness. To this dried mixture were then added 120 mg of phosphatidycholine, 40 mg of cholesterol and 8 mg of phosphatidylserine. The mixture was stirred gently to achieve a homogeneous solution and evaporated to dryness under $N_2$. The dried lipids were resuspended in 0.9% NaCl solution, hydrated for 112 hour in the dark and then sonicated in a cup-horn sonicator at 37° C. for 30 minutes. The non-entrapped was separated from liposomal encapsulated drug by extensive dialysis against 0.9% NaCl at 4° C. for 24 hours with at least 3 changes of saline solution. The percentage of entrapment of thalidomide in liposomes is determined spectrophometrically after the completion of dialysis.

EXAMPLE 12

Clinical Applications of the Invention

For patients who initially present without metastatic disease, thalidomide is used as an immediate initial therapy prior to surgery and radiation therapy, and as a continuous post-treatment therapy in patients at risk for recurrence or metastasis. The goal in these patients is to decrease the potential for metastatic cells from the primary tumor to develop into secondary tumors at other body sites.

For patients who initially present with metastatic disease, thalidomide is used as a continuous supplement to, or possible as a replacement for chemotherapy. The goal in these patients is to reduce or eliminate the possibility of metastases from primary tumors developing into secondary tumors at other body sites.

Thalidomide may be administered to a patient having prostate carcinoma at a dosage level of 750 mg once a day for a period of 10 days. The patient is monitored by observing the following parameters:

1. Tumor growth: x-rays and MRI and PET scans are used to determined if regression has occurred after one 10 day cycle of therapy.
2. Blood: the leukocyte count is observed between the 3rd and 5th days to see if there is an increase.
3. Liver function: urinalysis, serum creatinine and uric acid levels are monitored to determine toxicity.
4. The levels of the enzymes SGOT, SGPT, serum alkaline phosphatase are also determined.
5. Neurological side effects are also monitored during therapy.

It is to be understood that the forms of the invention herein are to be taken as preferred examples of the same and that various changes may be made without departing from the spirit of the invention or scope of the subjoined claims:

1. An enhanced pharmaceutical composition suitable for treating neoplastic diseases sensitive to said enhanced composition comprising:
   (a) an enhanced effective amount of thalidomide;
   (b) an effective amount of an alkylating agent selected from the group consisting of mechlorethamine, cyclophosphamide, ifosamide, melphalan, chlorambucil, busulfan, thiotepa, carmustine, lomustin, cisplatin, and carboplatin; and
   (c) a pharmaceutically acceptable inert carrier.

2. A method for the treatment of neoplastic diseases in a mammal which comprises administering to said afflicted mammal enhanced therapeutically-effective amounts of thalidomide in combination with effective amounts of other alkylating agent selected from the group consisting of mechlorethamine, cyclophosphamide, ifosamide, melphalan, chlorambucil, busulfan, thiotepa, carmustine, lomustin, cisplatin, and carboplatin wherein said neoplastic diseases are sensitive to said enhanced combination.

3. An enhanced pharmaceutical composition suitable for treating neoplastic diseases sensitive to said enhanced composition comprising:
   (a) an enhanced effective amount of thalidomide; and
   (b) an effective amount of an alkylating agent selected from the group consisting of mechlorethamine, cyclophosphamide, ifosamide, melphalan, chlorambucil, busulfan, thiotepa, carmustine, lomustin, cisplatin, and carboplatin.

* * * * *

UNITED STATES PATENT AND TRADEMARK OFFICE
CERTIFICATE OF CORRECTION

PATENT NO. : 6,140,346  
APPLICATION NO. : 09/071813  
DATED : October 31, 2000  
INVENTOR(S) : Peter J. Andrulis, Jr. et al.

Page 1 of 1

It is certified that error appears in the above-identified patent and that said Letters Patent is hereby corrected as shown below:

Title page at [63], "08/471,353" should read --08/471,351--.

In the Specification  
Column 1, line 6, "08/471,353" should read --08/471,351--.

Signed and Sealed this  
Nineteenth Day of November, 2013

Teresa Stanek Rea  
*Deputy Director of the United States Patent and Trademark Office*